United States Patent [19]

Jardieu

[11] Patent Number: 5,227,158
[45] Date of Patent: Jul. 13, 1993

[54] METHOD OF STIMULATING HEPATOCYTE PROLIFERATION BY ADMINISTRATION OF HEPATOCYTE GROWTH FACTOR AND GAMMA-INTERFERON

[75] Inventor: Paula M. Jardieu, Berkeley, Calif.

[73] Assignee: Genentech, Inc., South San Francisco, Calif.

[21] Appl. No.: 712,284

[22] Filed: Jun. 10, 1991

[51] Int. Cl.$^5$ .................... A61K 37/66; A61K 37/24; A61K 37/36
[52] U.S. Cl. .................................. 424/85.5; 514/12; 514/21; 530/399; 530/351
[58] Field of Search ................... 424/85.5; 514/12, 21; 530/399

[56] References Cited

U.S. PATENT DOCUMENTS

| | | | |
|---|---|---|---|
| 4,855,238 | 8/1989 | Gray et al. | 435/172.1 |
| 4,973,478 | 11/1990 | Gauldie et al. | 424/85.4 |
| 5,004,805 | 4/1991 | Gohda et al. | 530/399 |

OTHER PUBLICATIONS

Gauldie et al., *Proc. Natl. Acad. Sci.* USA 84, 7251 (1987).
Gohda et al., *J. Clin. Invest.* 81, 414 (1988).
Ichikara et al., *Mol. Cell. Biochem.* 43, 145 (1982).
McGowan et al., *J. Cell. Physiol.* 108, 353 (1981).
Michalopoulos et al., *Cancer Res.* 42, 4673 (1982).
Miyazawa et al., *Biochem. Biophys. Res. Comm.* 163, 967 (1989).
Nakamura et al., *J. Biochem.* (Tokyo) 94, 1029 (1982).
Nakamura et al., in *Proc. Natl. Acad. Sci.* USA 80, 7229 (1983).
Nakamura et al., *J. Biol. Chem.* 255, 7533 (1980).
Nakamura et al., *Biochim. Biophys. Acta* 678, 91 (1981).
Nakamura et al., *Nature* 342, 440 (1989).
Nakamura et al., *FEBS Letters* 224, 311 (1987).
Nakamura et al., *Biochem. Biophys. Res. Comm.* 122, 1450 (1984).
Noda et al., *J. Biol. Chem.* 258, 1520 (1983).
Richman et al., *Proc. Natl. Acad. Sci.* USA 73, 3589 (1976).
Seki, et al., *Biochem. Biophys. Res. Comm.* 172, 321 (1990).
Tanaka et al., *J. Biochem.* 84, 937 (1978).
Tomita et al., *Exp. Cell Res.* 135, 363 (1981).
Zarnegar and Michalopoulos, *Cancer Research* 49, 3314 (1989).
Zarnegar et al., *Biochem. Biophys. Res. Comm.* 163, 1370 (1989).
Quiroga et al. (1988) J. Interferon Res. 8:755-763.
Caselmann et al. (1989) Gastroenterology 96:449-455.

Primary Examiner—Robert A. Wax
Assistant Examiner—Richard C. Ekstrom
Attorney, Agent, or Firm—Ginger R. Dreger

[57] ABSTRACT

The invention relates to the synergistic interaction of hepatocyte growth factor (HGF) and gamma-interferon (IFN-γ) in the stimulation of hepatocyte growth. Accordingly, the invention concerns a method of enhancing the biological activity of HGF by administering a biologically effective amount of HGF and a synergistically effective amount of IFN-γ to a patient in need.

17 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4454 bases
( B ) TYPE: nucleic acid
( C ) STRANDEDNESS: single
( D ) TOPOLOGY: linear ( x i ) SEQUENCE DESCRIPTION: SEQ ID NO:1:

```
TTCGAGCTCG CCCGACATTG ATTATTGACT AGAGTCGATC GACAGCTGTG    50
GAATGTGTGT CAGTTAGGGT GTGGAAAGTC CCCAGGCTCC CCAGCAGGCA   100
GAAGTATGCA AAGCATGCAT CTCAATTAGT CAGCAACCAG GTGTGGAAAG   150
TCCCCAGGCT CCCCAGCAGG CAGAAGTATG CAAAGCATGC ATCTCAATTA   200
GTCAGCAACC ATAGTCCCGC CCCTAACTCC GCCCATCCCG CCCCTAACTC   250
CGCCCAGTTC CGCCCATTCT CCGCCCCATG GCTGACTAAT TTTTTTTATT   300
TATGCAGAGG CCGAGGCCGC CTCGGCCTCT GAGCTATTCC AGAAGTAGTG   350
AGGAGGCTTT TTTGGAGGCC TAGGCTTTTG CAAAAAGCTA GCTTATCCGG   400
CCGGGAACGG TGCATTGGAA CGCGGATTCC CCGTGCCAAG AGTCAGGTAA   450
GTACCGCCTA TAGAGTCTAT AGGCCCACCC CCTTGGCTTG GCCCACCCCC   500
TTGGCTTCGT TAGAACGCGG CTACAATTAA TACATAACCT TTTGGATCGA   550
TCCTACTGAC ACTGACATCC ACTTTTTCTT TTTCTCCACA GGTGTCCACT   600
CCCAGGTCCA ACTGCACCTC GGTTCGCGAA GCTAGCTTGG GCTGCATCGA   650
TTGAATTCCC CGGGGATCCT CTAGAGTCGA CCTGCAGAAG CTTCGATGGC   700
CGCCATGGCC CAACTTGTTT ATTGCAGCTT ATAATGGTTA CAAATAAAGC   750
```

```
AATAGCATCA CAAATTTCAC AAATAAAGCA TTTTTTTCAC TGCATTCTAG  800
TTGTGGTTTG TCCAAACTCA TCAATGTATC TTATCATGTC TGGATCGATC  850
GGGAATTAAT TCGGCGCAGC ACCATGGCCT GAAATAACCT CTGAAAGAGG  900
AACTTGGTTA GGTACCTTCT GAGGCGGAAA GAACCAGCTG TGGAATGTGT  950
GTCAGTTAGG GTGTGGAAAG TCCCCAGGCT CCCCAGCAGG CAGAAGTATG 1000
CAAAGCATGC ATCTCAATTA GTCAGCAACC AGGTGTGGAA AGTCCCCAGG 1050
CTCCCCAGCA GGCAGAAGTA TGCAAAGCAT GCATCTCAAT TAGTCAGCAA 1100
CCATAGTCCC GCCCCTAACT CCGCCCATCC CGCCCCTAAC TCCGCCCAGT 1150
TCCGCCCATT CTCCGCCCCA TGGCTGACTA ATTTTTTTA TTTATGCAGA 1200
GGCCGAGGCC GCCTCGGCCT CTGAGCTATT CCAGAAGTAG TGAGGAGGCT 1250
TTTTTGGAGG CCTAGGCTTT TGCAAAAAGC TGTTAACAGC TTGGCACTGG 1300
CCGTCGTTTT ACAACGTCGT GACTGGGAAA ACCCTGGCGT TACCCAACTT 1350
AATCGCCTTG CAGCACATCC CCCCTTCGCC AGCTGGCGTA ATAGCGAAGA 1400
GGCCCGCACC GATCGCCCTT CCCAACAGTT GCGTAGCCTG AATGGCGAAT 1450
GGCGCCTGAT GCGGTATTTT CTCCTTACGC ATCTGTGCGG TATTTCACAC 1500
CGCATACGTC AAAGCAACCA TAGTACGCGC CCTGTAGCGG CGCATTAAGC 1550
GCGGCGGGTG TGGTGGTTAC GCGCAGCGTG ACCGCTACAC TTGCCAGCGC 1600
CCTAGCGCCC GCTCCTTTCG CTTTCTTCCC TTCCTTTCTC GCCACGTTCG 1650
CCGGCTTTCC CCGTCAAGCT CTAAATCGGG GGCTCCCTTT AGGGTTCCGA 1700
TTTAGTGCTT TACGGCACCT CGACCCCAAA AAACTTGATT TGGGTGATGG 1750
TTCACGTAGT GGGCCATCGC CCTGATAGAC GGTTTTCGC CCTTTGACGT 1800
TGGAGTCCAC GTTCTTTAAT AGTGGACTCT TGTTCCAAAC TGGAACAACA 1850
CTCAACCCTA TCTCGGCTA TTCTTTTGAT TTATAAGGGA TTTTGCCGAT 1900
TTCGGCCTAT TGGTTAAAAA ATGAGCTGAT TTAACAAAAA TTTAACGCGA 1950
ATTTTAACAA AATATTAACG TTTACAATTT TATGGTGCAC TCTCAGTACA 2000
ATCTGCTCTG ATGCCGCATA GTTAAGCCAA CTCCGCTATC GCTACGTGAC 2050
TGGGTCATGG CTGCGCCCCG ACACCCGCCA ACACCCGCTG ACGCGCCCTG 2100
ACGGGCTTGT CTGCTCCCGG CATCCGCTTA CAGACAAGCT GTGACCGTCT 2150
CCGGGAGCTG CATGTGTCAG AGGTTTTCAC CGTCATCACC GAAACGCGCG 2200
AGGCAGTATT CTTGAAGACG AAAGGGCCTC GTGATACGCC TATTTTTATA 2250
GGTTAATGTC ATGATAATAA TGGTTTCTTA GACGTCAGGT GGCACTTTTC 2300
GGGGAAATGT GCGCGGAACC CCTATTTGTT TATTTTTCTA AATACATTCA 2350
AATATGTATC CGCTCATGAG ACAATAACCC TGATAAATGC TTCAATAATA 2400
TTGAAAAAGG AAGAGTATGA GTATTCAACA TTTCCGTGTC GCCCTTATTC 2450
CCTTTTTTGC GGCATTTTGC CTTCCTGTTT TTGCTCACCC AGAAACGCTG 2500
GTGAAAGTAA AAGATGCTGA AGATCAGTTG GGTGCACGAG TGGGTTACAT 2550
CGAACTGGAT CTCAACAGCG GTAAGATCCT TGAGAGTTTT CGCCCCGAAG 2600
AACGTTTTCC AATGATGAGC ACTTTTAAAG TTCTGCTATG TGGCGCGGTA 2650
TTATCCCGTG ATGACGCCGG GCAAGAGCAA CTCGGTCGCC GCATACACTA 2700
TTCTCAGAAT GACTTGGTTG AGTACTCACC AGTCACAGAA AAGCATCTTA 2750
CGGATGGCAT GACAGTAAGA GAATTATGCA GTGCTGCCAT AACCATGAGT 2800
```

```
GATAACACTG  CGGCCAACTT  ACTTCTGACA  ACGATCGGAG  GACCGAAGGA  2850
GCTAACCGCT  TTTTTGCACA  ACATGGGGGA  TCATGTAACT  CGCCTTGATC  2900
GTTGGGAACC  GGAGCTGAAT  GAAGCCATAC  CAAACGACGA  GCGTGACACC  2950
ACGATGCCAG  CAGCAATGGC  AACAACGTTG  CGCAAACTAT  TAACTGGCGA  3000
ACTACTTACT  CTAGCTTCCC  GGCAACAATT  AATAGACTGG  ATGGAGGCGG  3050
ATAAAGTTGC  AGGACCACTT  CTGCGCTCGG  CCCTTCCGGC  TGGCTGGTTT  3100
ATTGCTGATA  AATCTGGAGC  CGGTGAGCGT  GGGTCTCGCG  GTATCATTGC  3150
AGCACTGGGG  CCAGATGGTA  AGCCCTCCCG  TATCGTAGTT  ATCTACACGA  3200
CGGGGAGTCA  GGCAACTATG  GATGAACGAA  ATAGACAGAT  CGCTGAGATA  3250
GGTGCCTCAC  TGATTAAGCA  TTGGTAACTG  TCAGACCAAG  TTTACTCATA  3300
TATACTTTAG  ATTGATTTAA  AACTTCATTT  TTAATTTAAA  AGGATCTAGG  3350
TGAAGATCCT  TTTTGATAAT  CTCATGACCA  AAATCCCTTA  ACGTGAGTTT  3400
TCGTTCCACT  GAGCGTCAGA  CCCCGTAGAA  AAGATCAAAG  GATCTTCTTG  3450
AGATCCTTTT  TTTCTGCGCG  TAATCTGCTG  CTTGCAAACA  AAAAAACCAC  3500
CGCTACCAGC  GGTGGTTTGT  TTGCCGGATC  AAGAGCTACC  AACTCTTTTT  3550
CCGAAGGTAA  CTGGCTTCAG  CAGAGCGCAG  ATACCAAATA  CTGTCCTTCT  3600
AGTGTAGCCG  TAGTTAGGCC  ACCACTTCAA  GAACTCTGTA  GCACCGCCTA  3650
CATACCTCGC  TCTGCTAATC  CTGTTACCAG  TGGCTGCTGC  CAGTGGCGAT  3700
AAGTCGTGTC  TTACCGGGTT  GGACTCAAGA  CGATAGTTAC  CGGATAAGGC  3750
GCAGCGGTCG  GGCTGAACGG  GGGGTTCGTG  CACACAGCCC  AGCTTGGAGC  3800
GAACGACCTA  CACCGAACTG  AGATACCTAC  AGCGTGAGCA  TTGAGAAAGC  3850
GCCACGCTTC  CCGAAGGGAG  AAAGGCGGAC  AGGTATCCGG  TAAGCGGCAG  3900
GGTCGGAACA  GGAGAGCGCA  CGAGGGAGCT  TCCAGGGGGA  AACGCCTGGT  3950
ATCTTTATAG  TCCTGTCGGG  TTTCGCCACC  TCTGACTTGA  GCGTCGATTT  4000
TTGTGATGCT  CGTCAGGGGG  GCGGAGCCTA  TGGAAAAACG  CCAGCAACGC  4050
GGCCTTTTTA  CGGTTCCTGG  CCTTTTGCTG  GCCTTTTGCT  CACATGTTCT  4100
TTCCTGCGTT  ATCCCCTGAT  TCTGTGGATA  ACCGTATTAC  CGCCTTTGAG  4150
TGAGCTGATA  CCGCTCGCCG  CAGCCGAACG  ACCGAGCGCA  GCGAGTCAGT  4200
GAGCGAGGAA  GCGGAAGAGC  GCCCAATACG  CAAACCGCCT  CTCCCCGCGC  4250
GTTGGCCGAT  TCATTAATCC  AGCTGGCACG  ACAGGTTTCC  CGACTGGAAA  4300
GCGGGCAGTG  AGCGCAACGC  AATTAATGTG  AGTTACCTCA  CTCATTAGGC  4350
ACCCCAGGCT  TTACACTTTA  TGCTTCCGGC  TCGTATGTTG  TGTGGAATTG  4400
TGAGCGGATA  ACAATTTCAC  ACAGGAAACA  GCTATGACCA  TGATTACGAA  4450
TTAA  4454
```

( 2 ) INFORMATION FOR SEQ ID NO:2:

( i ) SEQUENCE CHARACTERISTICS:
        ( A ) LENGTH: 858 amino acids
        ( B ) TYPE: amino acid
        ( D ) TOPOLOGY: linear     ( x i ) SEQUENCE DESCRIPTION: SEQ ID NO:2:

```
Gly  Leu  Arg  Ala  Asp  Trp  Leu  Phe  Xaa  Ala  Leu  Thr  Pro  Asn  Arg
 1              5                   10                  15
```

-continued

| | | | | | | | | | | | | |
|---|---|---|---|---|---|---|---|---|---|---|---|---|
|Ile|Leu|Ser|Pro|Arg<br>20|His|Leu|Leu|Gln|Arg<br>25|Asp|Pro|Pro|Ala|Arg<br>30|
|Pro|Ala|Ala|Pro|Cys<br>35|Gly|Xaa|Pro|Asn|Ser<br>40|Cys|Gln|Pro|Cys|Cys<br>45|
|Cys|Ser|Met|Ser|Ser<br>50|Cys|Ile|Ser|Ser|Cys<br>55|Ser|Pro|Ser|Pro|Ser<br>60|
|Pro|Met|Gln|Arg|Asp<br>65|Lys|Gly|Lys|Glu|Glu<br>70|Ile|Gln|Phe|Met|Asn<br>75|
|Ser|Lys|Asn|Gln|Gln<br>80|Arg|Leu|Pro|Xaa|Ser<br>85|Lys|Xaa|Ile|Gln|His<br>90|
|Xaa|Arg|Xaa|Lys|Pro<br>95|Lys|Lys|Xaa|Ile|Leu<br>100|Gln|Thr|Asn|Val|Leu<br>105|
|Ile|Asp|Val|Leu|Gly<br>110|Ile|Lys|Asp|Phe|His<br>115|Ser|Leu|Ala|Arg|Leu<br>120|
|Leu|Phe|Leu|Ile|Lys<br>125|Gln|Glu|Asn|Asn|Ala<br>130|Ser|Gly|Ser|Pro|Ser<br>135|
|Ile|Ala|Cys|Gln|Val<br>140|Glu|Xaa|Lys|Lys|Asn<br>145|Leu|Ala|Met|Asn|Leu<br>150|
|Thr|Ser|Met|Lys|Thr<br>155|Lys|Thr|Thr|Leu|Glu<br>160|Thr|Ala|Ser|Leu|Val<br>165|
|Lys|Asp|Ala|Ala|Thr<br>170|Arg|Glu|Gln|Tyr|Leu<br>175|Ser|Leu|Arg|Val|Ala<br>180|
|Ser|Asn|Val|Ser|Pro<br>185|Gly|Val|Pro|Xaa|Tyr<br>190|His|Thr|Asn|Thr|Ala<br>195|
|Phe|Cys|Leu|Arg|Ala<br>200|Ile|Gly|Val|Lys|Thr<br>205|Tyr|Arg|Lys|Thr|Thr<br>210|
|Val|Glu|Ile|Leu|Glu<br>215|Gly|Lys|Lys|Gly|Asp<br>220|Pro|Gly|Val|Ser|Gln<br>225|
|Ala|Ile|Gln|Arg|Tyr<br>230|Ala|Thr|Lys|Ser|Val<br>235|Thr|Phe|Leu|Ser|Val<br>240|
|Gln|Lys|Leu|Asn|Ala<br>245|Xaa|Pro|Ala|Met|Gly<br>250|Arg|Val|Ile|Glu|Val<br>255|
|Ser|Trp|Ile|Ile|Gln<br>260|Asn|Gln|Ala|Arg|Phe<br>265|Val|Ser|Ala|Gly|Ile<br>270|
|Ile|Arg|His|His|Thr<br>275|Gly|Thr|Asn|Ser|Cys<br>280|Leu|Lys|Asp|Ile|Pro<br>285|
|Thr|Arg|Ala|Leu|Met<br>290|Ile|Ile|Ile|Ala|Ala<br>295|Ile|Pro|Met|Ala|Ser<br>300|
|Arg|Gly|His|Gly|Ala<br>305|Ile|Leu|Leu|Thr|Leu<br>310|Thr|Pro|Ala|Gly|Ser<br>315|
|Thr|Val|Gln|Leu|Lys<br>320|His|Ala|Leu|Thr|Ile<br>325|Leu|Xaa|Met|Thr|Leu<br>330|
|Met|Phe|Leu|Trp|Lys<br>335|Gln|Leu|Asn|Ala|Ser<br>340|Lys|Val|Lys|Glu|Lys<br>345|
|Ala|Thr|Gly|Ala|Leu<br>350|Ser|Ile|Pro|Phe|Gly<br>355|Met|Glu|Phe|His|Val<br>360|
|Ser|Val|Gly|Ile|Leu<br>365|Ser|Ile|Leu|Thr|Ser<br>370|Met|Thr|Xaa|Leu|Leu<br>375|
|Lys|Ile|Ser|Ser|Ala<br>380|Arg|Thr|Tyr|Glu|Lys<br>385|Ile|Thr|Ala|Glu|Ile<br>390|
|Gln|Met|Gly|Leu|Asn<br>395|His|Pro|Gly|Val|Leu<br>400|Pro|Leu|Ile|Gln|Thr<br>405|
|Ser|Glu|Leu|Ala|Thr<br>410|Ala|Pro|Lys|Phe|Gln<br>415|Thr|Val|Ile|Cys|His<br>420|
|Met|Asp|Lys|Ile|Val|Ile|Val|Gly|Met|Ala|Lys|Ile|Ile|Trp|Ala|

-continued

|   |   |   |   | 425 |   |   |   |   | 430 |   |   |   |   | 435 |
|---|---|---|---|---|---|---|---|---|---|---|---|---|---|---|
| Thr | Tyr | Pro | Lys | Gln | Asp | Leu | Asp | Xaa | His | Val | Gln | Cys | Gly | Thr |
|   |   |   |   | 440 |   |   |   |   | 445 |   |   |   |   | 450 |
| Arg | Thr | Trp | Lys | Thr | Tyr | Ile | Val | Ile | Ser | Ser | Gly | Asn | Gln | Met |
|   |   |   |   | 455 |   |   |   |   | 460 |   |   |   |   | 465 |
| Gln | Val | Ser | Xaa | Met | Arg | Ile | Thr | Ala | Glu | Ile | Gln | Met | Met | Met |
|   |   |   |   | 470 |   |   |   |   | 475 |   |   |   |   | 480 |
| Leu | Met | Asp | Pro | Gly | Ala | Thr | Arg | Glu | Ile | His | Ser | Phe | Leu | Gly |
|   |   |   |   | 485 |   |   |   |   | 490 |   |   |   |   | 495 |
| Ile | Ile | Ala | Leu | Phe | Leu | Val | Val | Lys | Val | Ile | Pro | His | Leu | Gln |
|   |   |   |   | 500 |   |   |   |   | 505 |   |   |   |   | 510 |
| Xaa | Ser | Ile | Xaa | Thr | Ile | Pro | Xaa | Tyr | Leu | Val | Pro | Lys | Arg | Asn |
|   |   |   |   | 515 |   |   |   |   | 520 |   |   |   |   | 525 |
| Asn | Cys | Glu | Leu | Xaa | Met | Gly | Phe | Gln | His | Glu | Gln | Thr | Xaa | Asp |
|   |   |   |   | 530 |   |   |   |   | 535 |   |   |   |   | 540 |
| Gly | Trp | Leu | Val | Xaa | Asp | Thr | Glu | Ile | Asn | Ile | Ser | Ala | Glu | Asp |
|   |   |   |   | 545 |   |   |   |   | 550 |   |   |   |   | 555 |
| His | Xaa | Xaa | Arg | Arg | Val | Gly | Phe | Leu | Leu | His | Asp | Ser | Val | Ser |
|   |   |   |   | 560 |   |   |   |   | 565 |   |   |   |   | 570 |
| Leu | Leu | Glu | Thr | Xaa | Lys | Ile | Met | Lys | Leu | Gly | Leu | Glu | Phe | Met |
|   |   |   |   | 575 |   |   |   |   | 580 |   |   |   |   | 585 |
| Met | Ser | Thr | Glu | Glu | Glu | Met | Arg | Asn | Ala | Asn | Arg | Phe | Ser | Met |
|   |   |   |   | 590 |   |   |   |   | 595 |   |   |   |   | 600 |
| Phe | Pro | Ser | Trp | Tyr | Met | Ala | Leu | Lys | Asp | Gln | Ile | Trp | Phe | Xaa |
|   |   |   |   | 605 |   |   |   |   | 610 |   |   |   |   | 615 |
| Xaa | Ser | Leu | Pro | Gly | Leu | Leu | Ser | Trp | Met | Ile | Leu | Leu | Val | Arg |
|   |   |   |   | 620 |   |   |   |   | 625 |   |   |   |   | 630 |
| Leu | Ile | Tyr | Leu | Ile | Met | Asp | Ala | Gln | Phe | Leu | Lys | Arg | Pro | Val |
|   |   |   |   | 635 |   |   |   |   | 640 |   |   |   |   | 645 |
| Ala | Val | Phe | Met | Ala | Gly | Ala | Thr | Leu | Asp | Xaa | Ser | Thr | Met | Met |
|   |   |   |   | 650 |   |   |   |   | 655 |   |   |   |   | 660 |
| Ala | Tyr | Tyr | Glu | Trp | His | Ile | Ser | Ile | Xaa | Trp | Glu | Met | Arg | Asn |
|   |   |   |   | 665 |   |   |   |   | 670 |   |   |   |   | 675 |
| Ala | Ala | Ser | Ile | Ile | Glu | Gly | Arg | Xaa | Leu | Xaa | Met | Ser | Leu | Lys |
|   |   |   |   | 680 |   |   |   |   | 685 |   |   |   |   | 690 |
| Tyr | Val | Leu | Gly | Leu | Lys | Arg | Leu | Asp | Gln | Asp | His | Val | Arg | Gly |
|   |   |   |   | 695 |   |   |   |   | 700 |   |   |   |   | 705 |
| Ile | Met | Val | Ala | His | Leu | Phe | Val | Ser | Asn | Ile | Lys | Xaa | Glu | Trp |
|   |   |   |   | 710 |   |   |   |   | 715 |   |   |   |   | 720 |
| Phe | Leu | Val | Ser | Leu | Phe | Leu | Val | Val | Asp | Val | Pro | Phe | Gln | Ile |
|   |   |   |   | 725 |   |   |   |   | 730 |   |   |   |   | 735 |
| Val | Leu | Val | Phe | Leu | Ser | Glu | Xaa | His | Ile | Met | Gln | Asn | Gly | Tyr |
|   |   |   |   | 740 |   |   |   |   | 745 |   |   |   |   | 750 |
| Thr | Lys | Leu | Phe | Xaa | His | Ile | Arg | Tyr | His | Ser | His | Ser | Xaa | Ser |
|   |   |   |   | 755 |   |   |   |   | 760 |   |   |   |   | 765 |
| Lys | Cys | Val | Xaa | Ser | Thr | His | Gln | Tyr | Asn | Cys | Leu | Leu | His | Glu |
|   |   |   |   | 770 |   |   |   |   | 775 |   |   |   |   | 780 |
| Asp | Phe | Arg | Glu | Cys | Gly | Ile | Xaa | Asn | Val | Thr | Tyr | Asn | Asn | Pro |
|   |   |   |   | 785 |   |   |   |   | 790 |   |   |   |   | 795 |
| Lys | Thr | Thr | Thr | Gly | Glu | Ser | Cys | Leu | Leu | Lys | Phe | Ser | Leu | Met |
|   |   |   |   | 800 |   |   |   |   | 805 |   |   |   |   | 810 |
| Phe | Met | Gly | Val | Phe | Cys | Cys | Phe | Val | Cys | Gln | Cys | Tyr | Phe | Val |
|   |   |   |   | 815 |   |   |   |   | 820 |   |   |   |   | 825 |
| Asn | Val | Glu | Val | Asn | Xaa | Gly | Thr | Cys | Lys | Cys | Asn | Asn | Ile | Ser |
|   |   |   |   | 830 |   |   |   |   | 835 |   |   |   |   | 840 |

```
Pro Glu Asp Thr Xaa Met Asp Xaa Lys Asn Thr Gln Val Tyr Leu
             845             850                     855
Leu Asp Asp
        858
```

METHOD OF STIMULATING HEPATOCYTE PROLIFERATION BY ADMINISTRATION OF HEPATOCYTE GROWTH FACTOR AND GAMMA-INTERFERON

FIELD OF THE INVENTION

The present invention concerns the hepatocyte growth factor-(HGF-) induced stimulation of hepatocyte regeneration. More particularly, the present invention relates to the synergistic interaction of HGF and gamma-interferon (IFN-γ) in such stimulation.

BACKGROUND ART

Liver damage occurs in a number of acute and chronic clinical conditions, including fulminant hepatic failure, hepatitis, partial hepatectomy, cirrhosis, hepatocyte transplant, transplant of artificial liver. In many instances, liver regeneration is vital to the survival of patients.

Liver cells have a good ability to regenerate. It is known that following partial hepatectomy, the liver size is usually restored to its exact original mass within about six days. Liver (hepatocyte) regeneration is believed to be controlled by various growth stimulatory and growth inhibitory cytokines of autocrine or paracrine origin, however, the exact role and action mechanism of these factors is far from entirely understood.

In vitro, DNA synthesis in isolated hepatocytes has been shown to be stimulated by growth factors such as insulin-like growth factor-I (IGF$_1$), epidermal growth factor (EGF), type α transforming growth factor (TGF-α) and to be inhibited by members of the type β transforming growth factor (TGF-β) family, and transferrin (activin). Most recently, a further protein, named hepatocyte growth factor (HGF) has been shown to be a complete mitogen for primary hepatocytes. The observation that the level of HGF in the serum rapidly increases following experimental damage to the liver and in patients with fulminate hepatic failure suggests that it may be an important mediator of liver regeneration in vivo.

HGF was purified by Nakamura et al. from the serum of partially hepatectomized rats [*Biochem. Biophys. Res. Comm.* 122:1450-1459 (1984)]. Subsequently, HGF was purified from rat platelets, and its subunit structure was determined [Nakamura et al, *Proc. Natl. Acad. Sci. USA.* 83. 6489-6493 (1986); and Nakamura et al., *FEBS Letters* 224, 311-316 (1987)]. The purification of human HGF (hHGF) from human plasma was first described by Gohda et al., *J. Clin. Invest.* 81, 414-419 (1988). According to the results reported by Gohda et al. hHGF is more effective in the stimulation of cultured hepatocyte proliferation than human epidermal growth factor (hEGF) or insulin, and the effect of hHGF with the maximal effects of hEGF and insulin is "additive or synergistic". Similarly, Zarnegar et al., *Cancer Research* 49, 3314-3320 (1989) described the purification of a polypeptide growth factor, called human hepatopoietin A (HPTA) having very similar properties to hHGF as characterized in earlier publications. As the authors do not disclose the amino acid sequences of their purified proteins, the degree of the structural similarity between the two factors can not be determined.

Using partial amino acid sequence generated from hHGF purified from human plasma, the molecular cloning and expression of hHGF, including the nucleotide sequence of hHGF cDNA and the deduced amino acid sequence of the hHGF protein, have been reported by Miyazawa et al., *Biochem. Byophys. Res. Comm.* 163, 967-973 (1989) and Nakamura et al., *Nature* 342, 440-443 (1989). The reported sequences differ in several positions. Nakamura et al., Supra describe the effect of hHGF and hEGF as being additive.

The N-terminal amino acid sequence of rabbit HPTA was described by Zarnegar et al., *Biochem. Biophys. Res. Comm.* 163, 1370-1376 (1989).

The hHGF cDNA encodes a 728 amino acids polypeptide (pre-pro hHGF) having a molecular mass ($M_r$) of about 82,000, and a heterodimeric structure, composed of a large α-subunit of 440 amino acids ($M_r$ 69,000) and a small β-subunit of 234 amino acids ($M_r$ 34,000). The nucleotide sequence of the hEGF cDNA reveals that both the α- and the β-chains are contained in a single open reading frame coding for a pre-pro precursor protein. In the predicted primary structure of mature hHGF, an interchain S-S bridge is formed between Cys 487 of the α-chain and Cys 604 in the β-chain (see Nakamura et al., Nature, Supra). The N-terminus of the α-chain is preceded by 54 amino acids, starting with a methionine group. This segment includes a signal sequence and the prosequence. The α-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α-chain. It will be understood that the definition of the various Kringle domains is based on their homology with kringle-like domains of other proteins (prothrombin, plasminogen), therefore, the above limits are only approximate. The HGF β-chain includes a serine-protease like domain. In a portion of cDNA isolated from human leukocytes in-frame deletion of 15 base pairs was observed. Transient expression of the cDNA sequence in COS-1 cells revealed that the encoded HGF molecule lacking 5 amino acids in the Kringle 1 domain was fully functional [Seki et al, *Biochem. and Biophys. Res. Commun.* 172, 321-327 (1990)]. This variant is referred to as "delta5 HGF". HGF contains four putative glycosylation sites, which are located at positions 294 and 402 of the α-chain and at positions 566 and 653 of the β-chain.

Gamma interferon (IFN-γ), which is also referred to as immune interferon, is a member of the interferon family, which exhibits the antiviral and anti-proliferative properties characteristic of interferons-α, and -β but, in contrast to those interferons, is pH 2 labile. IFN-γ was originally produced upon mitogenic induction of lymphocytes. The recombinant production of IFN-γ was first reported by Gray, Goeddel and coworkers [Gray et al., Nature 295, 503-508 (1982)], and is subject of U.S. Pat. Nos. 4,762,791, 4,929,544, 4,727,138 and 4,925,793. The recombinant IFN-γ of Gray and Goeddel as produced in *E. coli*, consisted of 146 amino acids, the N-terminal portion of the molecule commencing with the sequence CysTyrCys. It has later been found that the native IFN-γ (i.e., that arising from mitogen induction of human peripheral blood lymphocytes and subsequent purification) is a polypeptide which lacks the CysTyrCys N-terminus assigned by Gray et al., Supra.

It has previously been shown that IFN-γ exhibits a synergistic effect with IFN-α or IFN-β in assays for cells growth inhibition [EP 107,498, Czarnieski et al., *J. Virology* 49 (1984)], with lymphotoxin (EP 128,009), and with IL-2 (U.S. Pat. No. 5,082,658). Synergistic cytotoxic compositions comprising human interferon and TNF are disclosed in the U.S. Pat. No. 4,650,674.

SUMMARY OF THE INVENTION

We have found that although in certain clinical conditions resulting in liver damage, such as fulminate hepatic failure large concentrations of HGF were detected in the patients' sera, in many instances liver regeneration did not occur or was not satisfactory. In examining the effects of various proteins on the activity of recombinant HGF (rHGF), we have further found that IFN-γ synergizes with HGF to enhance the proliferation of primary rat hepatocytes.

The present invention is based on the recognition of the surprising synergism of HGF and IFN-γ, in particular in cooperating to enhance the proliferation of hepatocytes.

In one aspect, the present invention concerns a method of enhancing the biological activity of HGF by administering a biologically effective amount of HGF and a synergistically effective amount of IFN-γ to a patient in need.

In another aspect, the present invention concerns a method of enhancing hepatocyte proliferation comprising administering to a mammalian patient in need of such treatment and exhibiting elevated serum levels of endogenous hepatocyte growth factor (HGF), gamma interferon (IFN-γ) in an amount effective in inducing accelerated hepatocyte proliferation.

In still another aspect, the present invention relates to a method of enhancing the mitogenic activity of HGF on hepatocytes comprising administering to a mammalian patient in need of hepatocyte growth stimulation and exhibiting elevated serum levels of endogenous HGF, a synergistically effective amount of IFN-γ.

In a further aspect, the invention concerns a method of enhancing hepatocyte proliferation comprising administering to a mammalian patient in need of such treatment HGF in an amount effective in inducing hepatocyte proliferation and a synergistically effective amount of IFN-γ.

In a still further aspect, the present invention relates to a method for stimulating hepatocyte growth in a mammalian patient in need of such treatment, comprising:

a) determining the HGF concentration in the serum of said patient, b) comparing said HGF concentration with the normal HGF concentration in the serum of the same mammalian species, and c) administering a syngergistic amount of IFN-γ to said patient if said HGF concentration is higher than said normal HGF concentration, or e) administering a therapeutically effective amount of HGF and a synergistic amount of IFN-γ to said patient if said HGF concentration is the same or lower than said normal HGF concentration.

The present invention further relates to a composition for use in the stimulation of hepatocyte regeneration comprising a therapeutically effective amount of HGF and a synergistic amount of IFN-γ.

In a further aspect, the invention concerns a method for compensating the effect of growth inhibitors on HGF-induced hepatocyte proliferation, comprising administering to a mammalian patient in need of hepatocyte growth stimulation IFN-γ in an amount synergizing with HGF. The growth inhibitor is, for example, a member of the TGF-β superfamily.

DETAILED DESCRIPTION OF THE INVENTION

Hepatocyte growth factor (HGF) has been detected in a number of different tissues, including liver, lung, kidney brain, thymus, etc. Although HGF is primarily known as a potent mitogen for hepatocytes, its biological activity is not limited to hepatic cells. In in vitro tests, HGF has been found to be cytotoxic to mouse Sarcoma 180 cells and human mouth epidermal carcinoma (KB) cells [Higashiu et al., BBRC 170(1), 397–404, 1990], and mitogenic for various epithelial, endothelial and melanocyte cell lines. As used herein, the term "hepatocyte growth factor" or "HGF" is used to refer to all forms of hepatocyte growth factors that exhibit biological activity. The term specifically includes hepatocyte growth factors exhibiting hepatocyte growth promoting activity in standard assays, for example as described in *Proc. Natl. Acad. Sci. USA*. 80, 7229 (1983). The term specifically includes human and non-human, such as rat HGF, in mature, pre, pre-pro, or pro forms, purified from natural source, chemically synthesized or recombinantly produced.

The term "human hepatocyte growth factor" or "hHGF" refers to a polypeptide encoded by the cDNA sequence published by Miyazawa, et al., Supra, or Nakamura et al., Nature, Supra, including its single- and double-chain, mature, pre, pre-pro, and pro forms, purified from natural source, chemically synthesized or recombinantly produced (see also SEQ. ID. NO: 2). The sequences reported by Miyazawa et al. and Nakamura et al. differ in 14 amino acids. The reason for the differences is not entirely clear; polymorphism or cloning artifacts are among the possibilities. Both sequences are specifically encompassed by the term "hHGF" as defined for the purpose of the present invention. The term specifically includes "delta5 hHGF", a variant in which 5 amino acids are deleted in the first kringle domain of native human hHGF, which was first identified and described by Seki et al., Supra. Both terms ("HGF" and "hHGF") include various amino acid sequence variants of such HGF polypeptides, which may be naturally occurring alleles (which will not require manipulation of the HGF DNA) or predetermined mutant forms made by mutating the DNA, either to arrive to an allele or a variant not found in nature, provided that such variants maintain the biological activity in kind of native human HGF. Such mutations typically involve substitution, deletion and/or insertion of one or more amino acids in the native amino acid sequence. The amino acid changes also may result in further modifications of HGF upon expression in recombinant hosts, e.g. introducing or moving sites of glycosylation.

As used herein, "gamma interferon" or "IFN-γ" refers variously to all forms of (human and non-human animal) gamma interferon as are known to be biologically active in accepted gamma interferon assays, such as by inhibition of virus replication in a suitable cell line (inhibition of encephalomyocarditis virus replication in human lung carcinoma cell line A549 for human IFN-γ), induction of class II antigens, heat lability, other antiviral, antitumor or immunoregulatory assays, or neutralization by antibodies having immunoreactivity for gamma interferon but not alpha- or beta-interferon, and is meant to include gamma-interferon in a mature, pro, met or des(1-3) (also referred to as desCysTyrCys IFN-γ) form, whether obtained from natural source, chemically synthesized or produced by techniques of recombinant DNA technology. A complete description of the preparation of recombinant human gamma interferon (hIFN-γ) including its cDNA and amino acid sequences is shown in the United States Patents cited hereinabove (e.g. U.S. Pat. No. 4,762,791). CysTyrCys-lacking recombinant human gamma interferons, including variously truncated derivatives are, for example, disclosed in European Publication No. 146,354. Non-human animal interferons, including IFN-γ, are, for example, disclosed in European Publication No. 88,622. The term includes variously glycosylated forms and other variants and derivatives of such interferons, whether known in the art or will become available in the future. Examples of such variants are alleles, and the products of site directed mutagenesis in which residues are deleted, inserted and/or substituted (see, for example European Publication No. 146,354 referred to above).

IFN-γ is known to have a narrow host range, therefore, IFN-γ homologous to the animal to be treated should be used. In human therapy, the desCysTyrCys variant of the sequence shown, for example, in U.S. Pat. No. 4,717,138, and its counterpart EP 77,670 is preferably employed, and optionally the C-terminal variant in which the last 4 residues are deleted in post-translational processing.

The terms "synergism", "synergistic", synergistically effective" in the context of this invention are defined according to the art accepted definition (Goodman et al., "The Pharmacological Basis of Therapeutics", MacMillan Publishing Company, Inc., New York, 1980). This is most easily seen in terms of constructing an isobologram which plots the dosage levels required for a specific identical biological response of each of two ingredients along the X and Y axes. While simply additive effects would generate a straight line as one ingredient diminishes and the other increases, synergistic effects can be recognized by the generation of a concave curve, such that only a small increase in one component compensates for a drastic decrease in the amount of the other.

In a pharmacological sense, in the context of the present invention, a "therapeutically effective amount" or HGF refers to an amount effective in stimulating hepatocyte DNA synthesis in the presence of a synergistic amount of IFN-γ.

The term "hepatocyte growth inhibitor" is used to refer to factors inhibiting hepatocyte growth in vivo or in vitro in standard assays, such as those based upon monitoring hepatocyte DNA synthesis or liver weight. The term "hepatocyte growth inhibitor" specifically includes members of the TGF-β superfamily, e.g. TGF-β and activin (dimers of inhibin beta$_A$ or beta$_B$ chains).

The term "TGF-β" as used throughout the specification and claims includes various sub-types of TGF-β, e.g. TGF-β$_1$, -β$_2$ and -β$_3$ having hepatocyte growth inhibitory effect.

Hepatocyte proliferation and the effect of growth promoting and growth inhibiting factors are conveniently tested in primary cultures of hepatocytes. Adult rat hepatocytes in primary culture have been extensively used to search for factors that regulate hepatocyte proliferation, accordingly, techniques for isolating and culturing rat hepatocytes are well known in the art. Human hepatocytes can, for example, be obtained from whole liver perfusion on organs deemed unacceptable for transplantation, pare-downs of adult livers used for transplantation in children, fetal livers and liver remnants removed at surgery for other indications. Human hepatocytes can be cultured similarly to the methods established for preparing primary cultures of normal rat hepatocytes.

Hepatocyte DNA synthesis can, for example, be assayed by measuring incorporation of [$^3$H]thymidine into DNA, with appropriate hydroxyurea controls for replicative synthesis. Nuclear labelling is confirmed by autoradiography. A method for measuring hepatocyte DNA synthesis in primary culture of hepatocytes with or without aphidicolin is described by Nakamura et al., in *Biochem. Biophys. Res. Comm.* 122(3), 140-1459 (1984), and in *J. Biochem.* 94, 1029-1035 (1983). A modified version of this technique is disclosed in the Example.

The effect of HGF and IFN-γ on hepatocyte growth can also be tested in animal models of liver dysfunction and regeneration, such as in rats following partial hepatectomy, or carbon tetrachloride caused hepatic injury, in D-galactosamine induced acute liver failure models, etc.

IFN-γ and HGF are usually administered in the form of pharmaceutical compositions comprising an effective amount of the active ingredient in admixture with a suitable pharmaceutically acceptable vehicle and optionally other pharmaceutically acceptable additives.

The term "pharmaceutical composition" refers to preparations which are in such form as to permit the biological activity of the active ingredients to be unequivocally effective, and which contain no additional components which are toxic to the subjects to which the composition would be administered.

"Pharmaceutically acceptable" excipients (vehicles, additives) are those which can reasonably be administered to a subject mammal to provide an effective dose of the active ingredient employed.

HGF and IFN-γ may be administered to a subject mammal, preferably human, via any of the accepted modes of administration for agents which exhibit such activity. These methods include subcutaneus and, preferably, parenteral administration. Examples of parenteral administration routes are intravenous, intrapulmonary, intraarterial, intramuscular, and intraperitoneal administration, the intravenous route being preferred. Administration may be continuous or bolus dosing in sufficient amounts to maintain therapeutically effective/synergistic levels.

HGF and IFN-γ may be combined in vitro before administration or separately administered simultaneously or in tandem, in either order.

The compounds are usually administered as pharmaceutical compositions, usually formulated in dosage forms by methods known in the art; for example, see Remington's Pharmaceutical Sciences, Mack Publishing Company, Easton, Pa., 15th Edition 1975. For parenteral administration, HGF and IFN-γ are typically formulated in the form of injectable solutions, suspensions or emulsions, in admixture with a suitable pharmaceutically acceptable vehicle and optionally other pharmaceutically acceptable additives. Typical vehicles include saline, dextrose solution, Ringer's solution, etc., but non-aqueous vehicles may also be used.

The formulation of IFN-γ is preferably liquid, and is ordinarily a physiological salt solution or dextrose solution, together with conventional stabilizers and/or excipients. IFN-γ compositions may also be provided as lyophilized powders. A typical formulation may contain IFN-γ ($20 \times 10^6$ U) at 1.0 or 0.2 mg/ml, 0.27 mg/ml succinic acid, and disodium succinate hexahydrate 0.73 ml/injection at pH 5.0. Preferred IFN-γ formulations are disclosed in co-pending U.S. Pat. Ser. No 07/514,392, filed Apr. 25, 1990.

The determination of the synergistically effective amounts and the amounts effective in inducing accelerated hepatocyte proliferation is well within the skill of the practicing physician. The actual dose for both HGF and IFN-γ will depend on the medical condition to be treated, the pathological condition and clinical tolerance of the patient involved, the properties of the IFN-γ and HGF preparations employed, including their activity and biological half-life, etc. It will be appreciated that the practitioner will adjust the dose in line with clinical experience.

In order to simplify the following example, the definitions of certain terms is given hereinbelow.

"Transfection" refers to the taking up of an expression vector by a host cell whether or not any coding sequences are in fact expressed. Numerous methods of transfection are known in the art, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride as described by Cohen, S.N. *Proc. Natl. Acad. Sci. USA* 69, 2110 (1972); Mandel et al., *J. Mol. Biol.* 53, 154 (1970); and more recently Liljestrom et al., *Gene* 40, 241–246 (1985), is generally used for prokaryotes or other cells that contain substantial cell-wall barriers. For mammalian cells without such cell walls, the calcium phosphate precipitation method of Graham, F. and van der Eb, A., *Virology* 52, 456–457 (1978) is preferred. General aspects of mammalian host cell system transformations have been described by Axel in U.S. Pat. No. 4,399,216 issued Aug. 16, 1983. Transformations in yeast are typically carried out according to the method of Van Solingen, P., et al., *J. Bact.* 130, 946 (1977), and Hsiao, C.L. et al., *Proc. Natl. Acad. Sci. USA* 76, 3829 (1979). However, other methods for introducing DNA into cells such as by nuclear injection or by protoplast fusion may also be used.

"Plasmids" are designated by lower case p followed by capital letters and/or numbers. The starting plasmids used in the construction of the expression plasmid described in the Example are commercially, available, are publicly available on an unrestricted basis, or can be constructed from such available plasmids in accord with published procedures. In addition, other equivalent plasmids are known in the art, and will be apparent to the ordinary artisan.

Expression vectors (plasmids) may contain a selection gene, also termed a selectable marker. A selection gene encodes a protein, sometimes referred to as a secondary protein, necessary for the survival or growth of a host cell transformed with the vector. Examples of suitable selectable markers for mammalian cells are dihydrofolate reductase (DHFR), thymidine kinase or neomycin. When selectable markers are successfully transferred into a mammalian host cell, the transformed mammalian host cell can survive if placed under selective pressure. There are two widely used distinct categories of selective regimens. The first category is based on a cell's metabolism and the use of a mutant cell line which lacks the ability to grow independent of a supplemented media. Two examples are: CHO dhfr− cells and mouse ltk− cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media. Therefore, direct selection of those cells requires cell growth in the absence of supplemental nutrients.

A second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Mol. Appl. Genet.* 1, 327 (1982), mycophenolic acid, Mulligan, R.C. and Berg, P., *Science* 209, 1422 (1980), or hygromycin, Sugden, B. et al., *Mol. Cel., Biol.* 5, 410–413 (1985). In the following Example the direct selection for DHFR production was used.

"Amplification" refers to the increase or replication of an isolated region within a cell's chromosomal DNA. Amplification is achieved using a selection agent, e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater MTX to the media. Amplification of a desired gene can be achieved by cotransfecting a mammalian host cell with a plasmid having a DNA encoding a desired protein and the DHFR or amplification gene so that cointegration can occur. One ensures that the cell requires more DHFR, which requirement is met by replication of the selection gene, by selecting only for cells that can grow in successive rounds of ever-greater MTX concentration. So long as the gene encoding a desired heterologous protein has cointegrated with the amplifiable gene, replication of this gene gives rise to replication of the gene encoding the desired protein. The result is that increased copies of the gene, i.e. an amplified gene, encoding the desired heterologous protein express more of the desired heterologous protein. Essentially this procedure was followed during the hHGF expression, as shown in the following Example.

Suitable host cells for expressing the hHGF encoding DNA include: monkey kidney CVI line transformed by SV40 (COS-7m ATCC CRL 1665); human embryonic kidney line (293, Graham, F.L. et al., *J. Gen. Virol.* 36, 59 (1977)); baby hamster kidney cells (BHK, ATCC CCL 10)1 chinese hamster ovary-cells-DHFR (described by Urlaub and Chasin, *Proc. Natl. Acad. Sci. USA* 77, 4216 (1980), etc.

The host cells may be transformed with hHGF expression vectors and cultured in conventional nutrient media modified as is appropriate for inducing promoters, selecting transformants or amplifying genes. The culture conditions, such as temperature, pH and the like, are those previously used with the host cell selected for expression, and will be apparent to the ordinary skilled artisan.

Further details of the invention are illustrated in the following non-limiting example.

EXAMPLE

A. Recombinant production of hHGF

Figure 6:
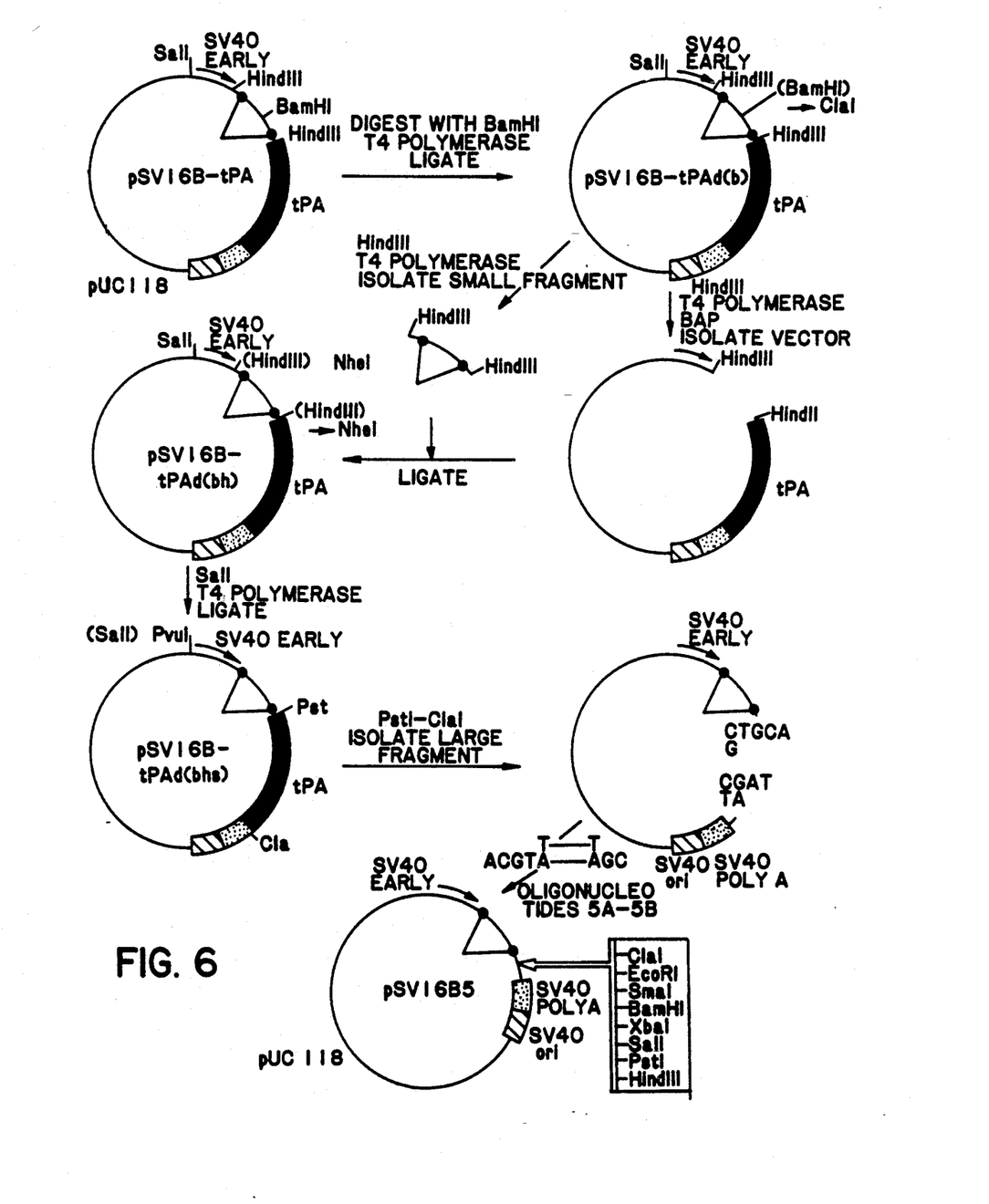
FIG. 6 shows the construction of the general expression vector pSVI6B5 into which any gene encoding a desired polypeptide may be conveniently inserted.

The plasmid pSVI6B5, which is a broadly applicable parental vector for expression of different polypeptides was derived from plasmid pSVI6B-tPA, as shown in FIG. 6. pSVI6B5 (transformed *E. coli* strain ATCC No. 68,151; SEQ. ID. NO: 1) carries polylinker regions in place of the t-PA cDNA in pSVI6B-tPA. These polylinker regions provide convenient, unique restriction endonuclease recognition sites that can be used to introduce any sequence that encodes a polypeptide of interest.

As illustrated in FIG. 6, pSVI6B5 was generated in four steps. The first three steps involved the removal of the BamHI, HindIII, and SalI restriction sites, respectively, from pSVI6B-tPA; as a consequence, upon replacement of the t-PA cDNA by the polylinker in the last step, the polylinker sites for these enzymes were unique in the resulting parental expression plasmid. A detailed description of the construction of pSVI6B5 is provided in application Ser. No. 07/441,514, filed Nov. 22, 1989, now abandoned.

An hHGF cDNA clone (HLC3) isolated from a human leukocyte library as described by Seki et al., Supra, was cloned into the expression vector pSVI6B5. The complete amino acid sequence of human leukocyte HGF is shown as SEQ. ID. NO: 2.

CHO-dhfr$^-$ cells (Urlaub et al., *Proc. Natl. cad. Sci. USA* 77, 4216–4220 (1980)) Were contransfected with the above-described pSVI6B5-based hHGF expression vector and with a dhfr selection vector pFD11 (Simonsen and Levinson, *Proc. Natl. Acad. Sci. USA* 80, 2495–2499 (1983)) using the general procedure of Graham and van des Eb, *Virology* 52, 456–467 (1973)). The latter plasmid encodes DHFR, thereby conferring methotrexate resistance on the transfected cells and allowing for selection of hHGF expressing transformants. The transformed dhfr$^-$ cells were selected by growth in glycine-, hypoxanthine- and thymidine-deficient medium. Colonies that arose on this selection medium were isolated using cotton swabs and propagated in the same medium to several generations. After cell growth, the cells were amplified and selected with increasing amounts of methotrexate using standard techniques. Clones that could grow in selective media, and therefore incorporated the transfected DHFR containing plasmid, were screened for the presence of secreted HGF. HGF activity in the media of these clones was assayed with the mitogenic assay described hereinbelow. Alternatively, HGF activity in culture media may also be measured by incorporation of $^{125}$I-labelled deoxyuridine into rat hepatocyte in primary culture as described by Nakamura et al., Nature 342, 440–443 (1989). hHGF was purified essentially as described by Nakamura et al., Supra.

B. Hepatocyte Growth Factor Bioassay

HGF activity was assayed essentially following the method described by Nakamura et al. in *Proc. Natl. Acad. Sci. USA* 80, 7229 (1983).

The assay media had the following composition:
Williams Media E (Gibco)
1×Pen/Strep (100 Units/ml penicillin - 100 μg/ml streptomycin)
1×glutamine (2 mM)
1×trace elements (10,000×stock from Phase 7)
10 μg/ml transferrin
1 μg/ml aprotinin Hepatocytes were isolated and purified from Wistar rats weighing 150–180 grams each, by method of standard perfusion collagenase [Seglen, P.O., *Methods in Cell Biology* 13, 29–83 (1976)], washed in assay media 3×, and resuspended in the assay media at a concentration of 1×10$^5$ cells/ml. 100 μl of the cell suspension were added to each well of a 96 well flat bottom microtiter plate. Appropriate dilutions of HGF or an other test compound were added to the cells in 100 μl volumes. The plates were incubated at 37° C. for 48 hours. The rate of DNA synthesis was determined by pulse-labeling cultured cells with $^3$H-thymidine (1 μCi/well) for 12 hours. The cells were then harvested onto glass fiber filters using automated cell harvester (Ph D harvester, Cambridge Biotech), the glass fiber filters were transferred to counting vials, and $^3$H incorporation expressed in cpms, was measured using liquid scintillation spectrometry.

C. Results

Figure 1:
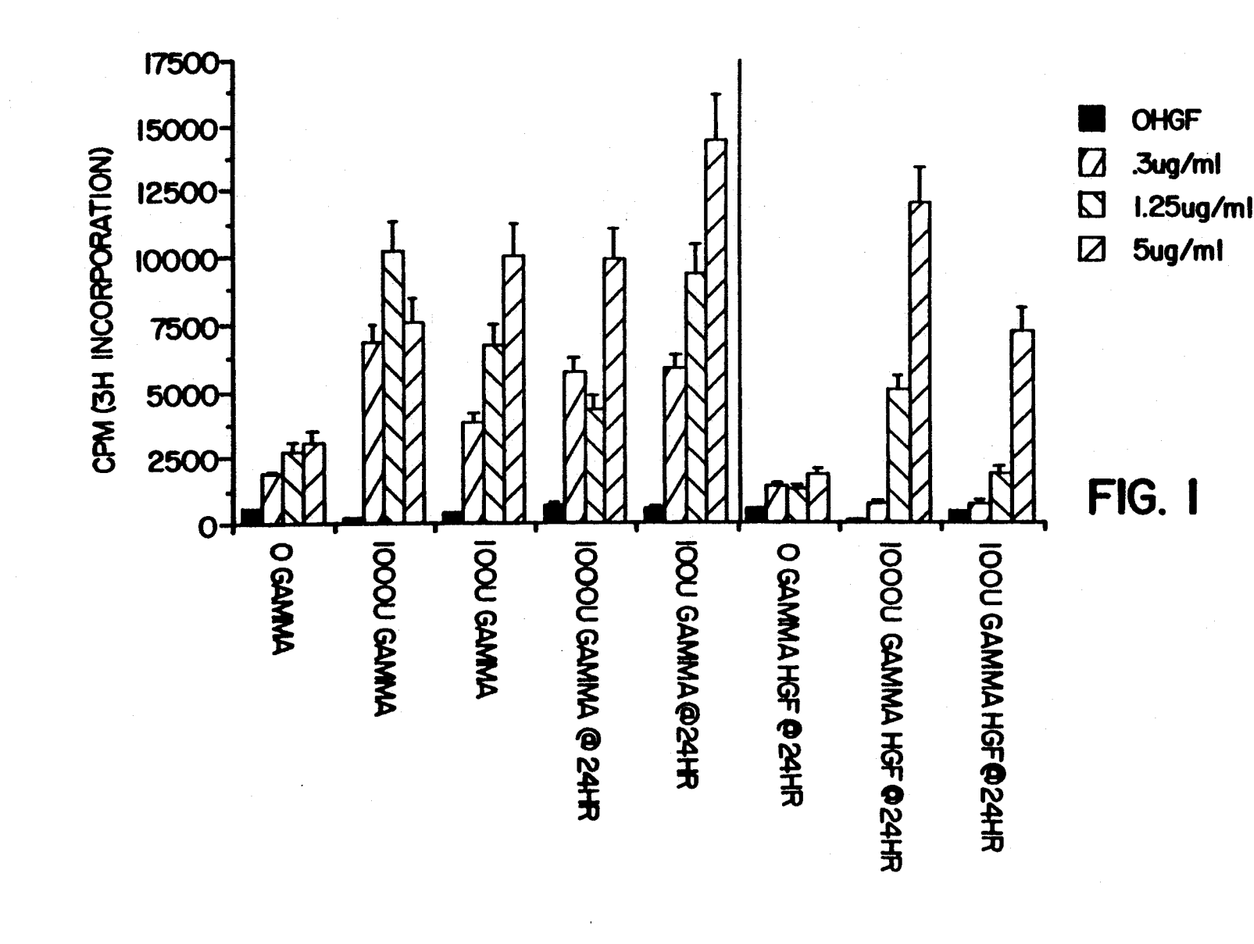
FIG. 1 illustrates the synergistic effect of IFN-γ and HGF to increase hepatocyte proliferation in primary rat hepatocyte cell cultures.

1. We have examined the effects of IFN-γ on hepatocyte proliferation. The results set forth in FIG. 1 show that IFN-γ alone has no mitogenic effect. Various combinations of HGF and IFN-γ were found to act synergistically in enhancing hepatocyte proliferation in the above-described primary rat hepatocyte cell cultures. The effect of tandem administration or HGF and IFN-γ has also been investigated. As shown in FIG. 1, the synergy was independent of time of addition of either HGF or IFN-γ.

Figure 2A:
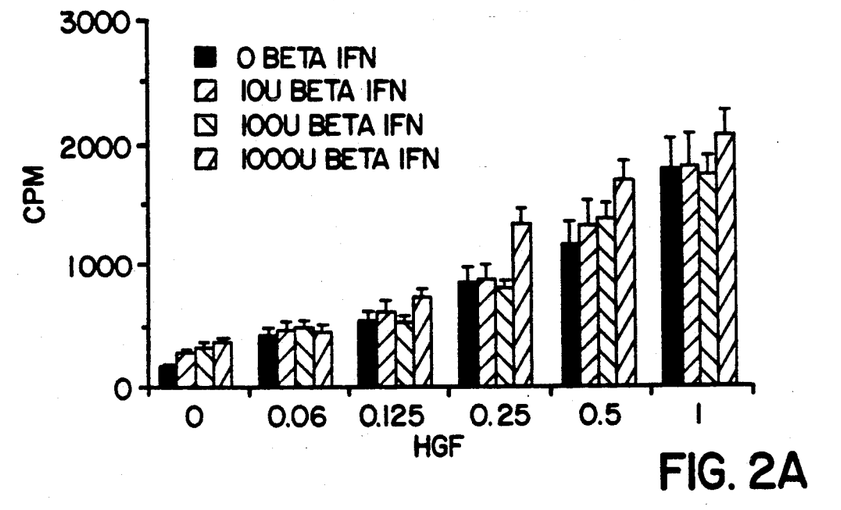
FIG. 2 shows the results obtained with IFN-β and IFN-α and HGF under similar conditions to those shown in FIG. 1.
Figure 2B:
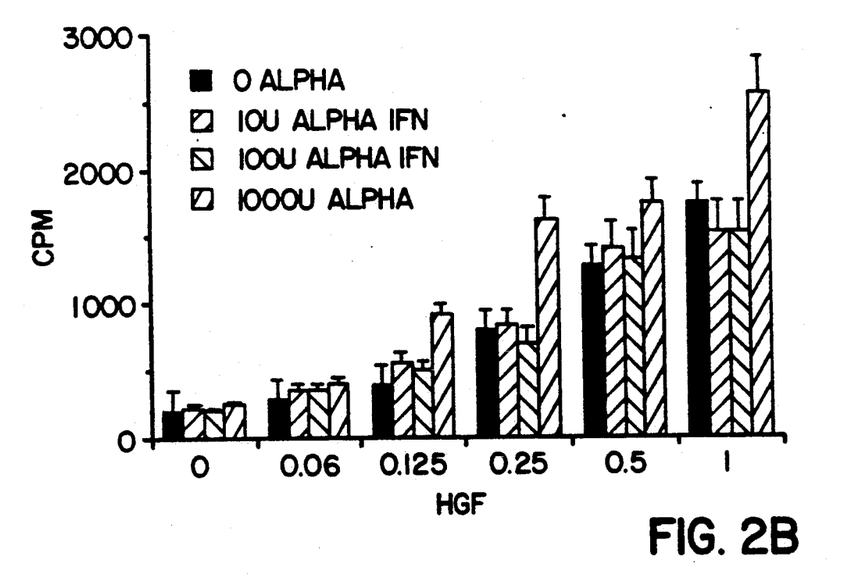
Figure 3:
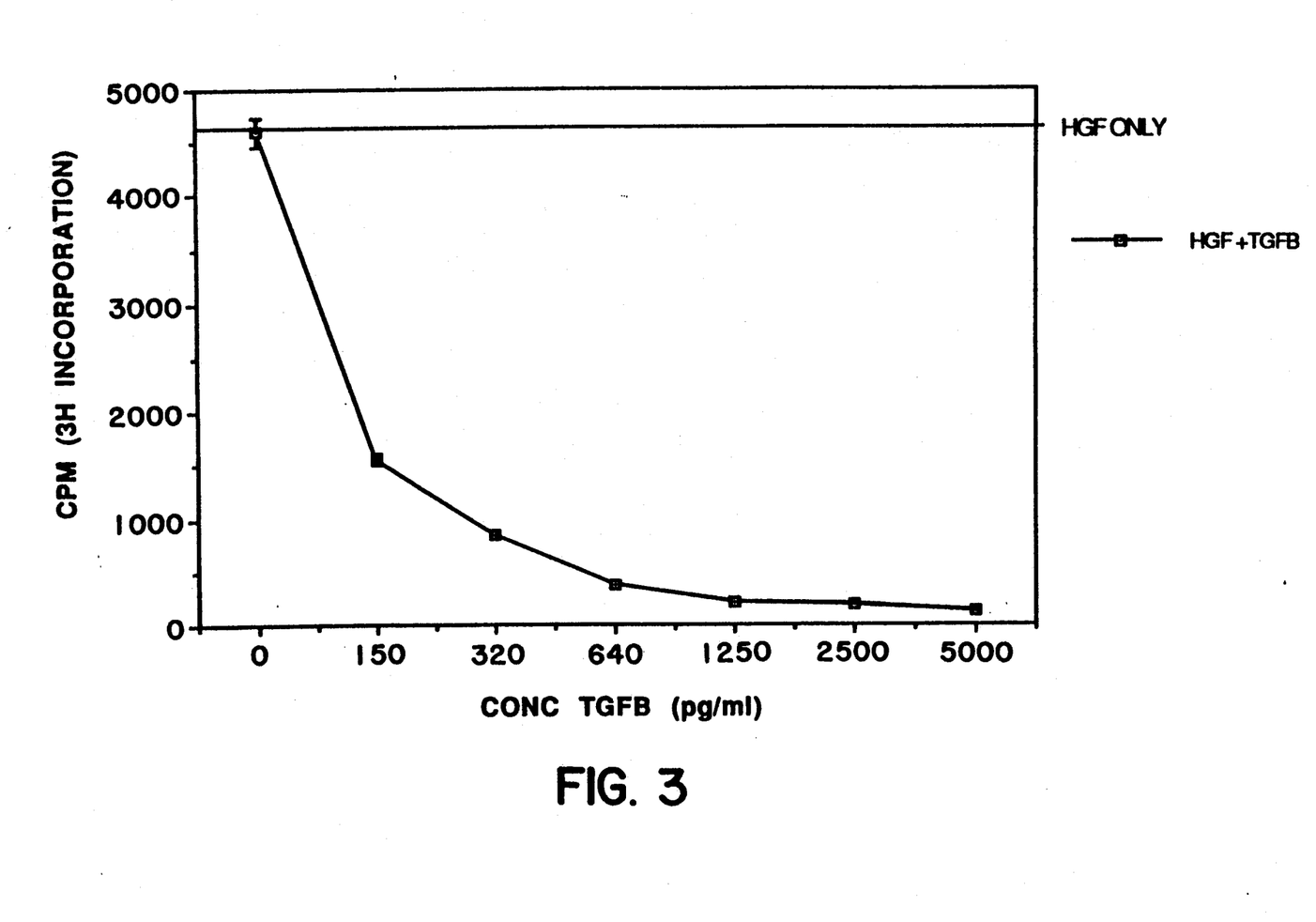
FIG. 3 illustrates the inhibitory effect of TGF-β on HGF induced proliferation of hepatocytes.

2. The test results illustrated in FIGS. 2 and 3 show that IFN-β failed to synergize with HGF, whereas the synergism between IFN-α and HGF was, at best, marginal.

3. It was found that as little as 150 pg of TGF-β, added at the initiation of culture, produced profound suppression of the HGF induced proliferation of primary rat hepatocytes (FIG. 3).

Figure 4:
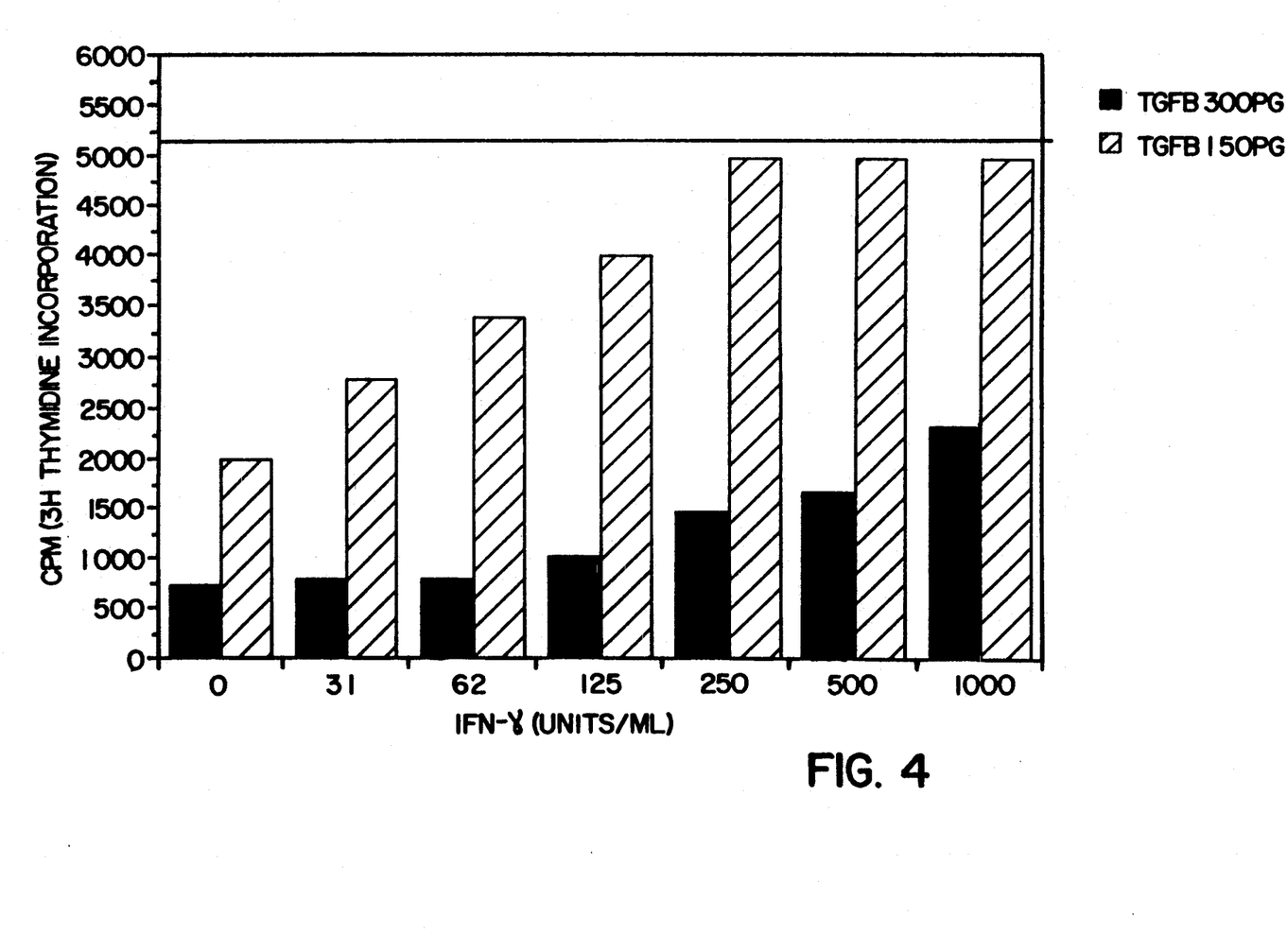
FIG. 4 illustrates the effect of IFN-γ on TGF-β inhibition of HGF activity.

4. As shown in FIG. 4, 250 U (100 ng) of IFN-γ completely reversed the suppressive effect of 150 pg TGF-β. Higher concentrations of IFN-γ were required to overcome the effect of higher concentrations of TGF-β.

Figure 5:
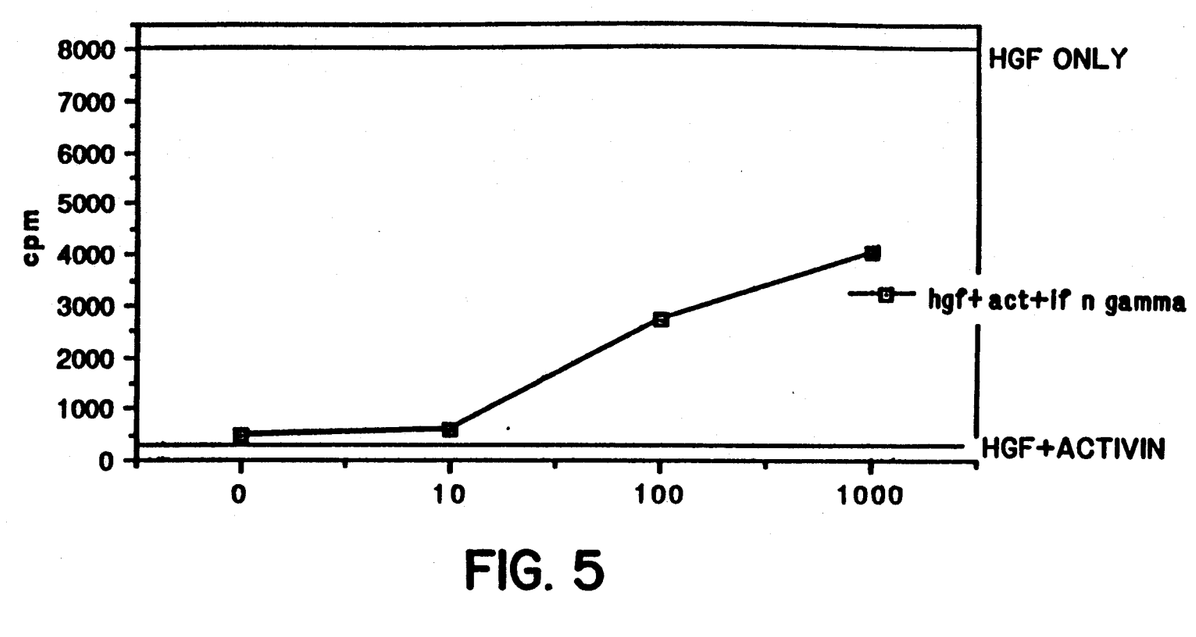
FIG. 5 illustrates the effect of IFN-γ on the inhibition of HGF activity by activin.

5. As illustrated in FIG. 5, the suppressive effect of activin, another member of the TGF-β family, was also reversed by IFN-γ. In this experiment, the activin concentration was 10 ng/ml, and the IFN-γ concentration varied between 0 and 1000 units/ml. The results show that at concentrations exceeding about 10 units/ml, IFN-γ reversed the suppressive effect of activin, and enhanced the hepatocyte growth stimulating activity of HGF.

E. coli 294 strain transformed with the plasmid PSVI6B5 has been deposited with the American Type Culture Collection, 12301 Parklawn Drive, Rockville, Md., USA (ATCC) on Oct. 25, 1989, and was assigned the ATCC Accession No. 68,151. The deposit was made under the provisions of the Budapest Treaty on the International Recognition of the Deposit of Microorganisms for the Purpose of Patent Procedure, and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. 112 and the Commissioner's rules pursuant thereto (including 37 CFR 1.14 with particular reference to OG 638).

The foregoing written description is considered to be sufficient to enable one skilled in the art to practice the invention. The deposit of material herein does not constitute an admission that the written description is inadequate to enable the practice of any aspect of the invention, including the best mode thereof, nor is it to be construed as limiting the scope hereof.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

All citations cited throughout the specification and the references cited therein, are hereby expressly incorporated by reference.

I claim:

1. A method of enhancing hepatocyte proliferation comprising administering to a mammalian patient in need of such treatment exogenous native sequence human hepatocyte growth factor (hHGF) in an amount effective in inducing hepatocyte proliferation and a synergistically effective amount of gamma interferon (IFN-γ).

2. The method of claim 1 wherein said exogenous hHFG is administered prior to IFN-γ administration.

3. The method of claim 1 wherein said exogenous hHFG is administered following IFN-γ administration.

4. The method of claim 1 wherein said exogenous hHFG and IFN-γ are administered simultaneously.

5. The method of claim 4 wherein said exogenous hHFG and IFN-γ are administered in a single pharmaceutical composition in admixture with at least one pharmaceutically acceptable excipient.

6. The method of claim 1 wherein said patient was subject to acute or chronic liver injury.

7. The method of claim 6 wherein said patient is human and said IFN-γ is human IFN-γ.

8. The method of claim 7 wherein said IFN-γ is human desCysTyrCys IFN-γ.

9. The method of claim 7 wherein said patient was subject to partial hepatectomy.

10. The method of claim 9 wherein said human IFN-γ is administered within about 6 days following partial hepatectomy.

11. The method of claim 10 wherein said human IFN-γ is administered within about 24 hours following partial hepatectomy.

12. The method of claim 10 wherein said human IFN-γ is administered as a liquid pharmaceutical formulation.

13. A method of stimulating hepatocyte growth in a mammalian patient in need of such treatment, comprising:
  a) determining the hepatocyte growth factor (HGF) concentration in the serum of said patient,
  b) comparing said HGF concentration with the normal HGF concentration in the serum of the same mammalian species, and
  c) administering a synergistic amount of IFN-γ to said patient if said HGF concentration is higher than said normal HGF concentration, or
  e) administering a therapeutically effective amount of native sequence human hepatocyte growth factor (hHGF) and a synergistic amount of IFN-γ to said patient if said HGF concentration is the same or lower than said normal HGF concentration.

14. A composition for use in the stimulation of hepatocyte regeneration comprising a therapeutically effective amount of native sequence human hepatocyte growth factor (hHGF) and a synergistic amount of gamma interferon (IFN-γ).

15. The composition of claim 14 comprising from about 100 U to about 1000 U of IFN-γ.

16. The composition of claim 15 further comprising at least one pharmaceutically acceptable excipient.

17. A method of enhancing the hepatocyte growth stimulating activity of hepatocyte growth factor (HGF), comprising administering to a mammalian patient native sequence human hepatocyte growth factor (hHGF) and a synergistically effective amount of gamma interferon (IFN-γ).

* * * * *